United States Patent
Yoo et al.

(10) Patent No.: US 7,314,946 B2
(45) Date of Patent: Jan. 1, 2008

(54) (2-CYCLOPENTENYL)CHLOROSILANES AND THEIR PREPARATION METHODS

(75) Inventors: Bok Ryul Yoo, Seoul (KR); Joon Soo Han, Seongnam-si (KR); Weon Cheol Lim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/634,732

(22) Filed: Dec. 6, 2006

(65) Prior Publication Data

US 2007/0191622 A1    Aug. 16, 2007

(30) Foreign Application Priority Data

Feb. 15, 2006   (KR) ...................... 10-2006-0014587

(51) Int. Cl.
*C07F 7/08* (2006.01)
(52) U.S. Cl. ...................................... 556/481; 556/481
(58) Field of Classification Search .................. 556/481
See application file for complete search history.

(56) References Cited

FOREIGN PATENT DOCUMENTS

| CS | 171581 B | 10/1976 |
|----|----------|---------|
| CS | 171582 B | 10/1976 |
| JP | 53-105464 | 9/1978 |
| JP | 2002-226407 | 8/2002 |

OTHER PUBLICATIONS

Vaisarova, V. and Hetflejs. J.: "Palladium- and Nickel-Catalysed Hydrosilylation of Cyclopentadiene". *Collection Czechoslov. Chem Commun.* vol. 41 (1976), pp. 1906-1913.
Hayashi, Tamio; Matsumoto, Yonetatsu; Morikawa, Ikutaro; Ito, Yoshihiko: "Catalytic Asymmetric Hydrosilylation of 1.3-Dienes with New Chiral Ferrocenylphosphine-Palladium Complexes", *Tetrahedron Asymmetry*, vol. 1. No. 3. (1990) pp. 151-154.
Marinetti, Angela: "An Investigation into a Palladium Catalyzed Hydrosilylation of Olefins", *Tetrahedron Letters*. vol. 35, No. 32 (1994) pp. 5861-5864.
Kiso Yoshihisa; Yamamoto, Keiji; Tamao, Kohei; Kumada, Makoto: "Asymmetric Homogeneous Hydrosilylation with Chiral Phosphine-Palladium Complexes", *Journal of the American Chemical Society*, vol. 94, No. 12 (Jun. 14, 1972) pp. 4373-4374.
Yamamoto, Keiji; Kiso, Yoshihisa; Ito, Ryuichi; Tamao, Kohei, Kumada, Makoto: "Catalytic Asymmetric Hydrosilylation of Olefins III. Chiral Phosphine-Palladium (II) Complexes as Hydrosilylation Catalysts", *Journal of Organometallic Chemistry*, vol. 210 (1981) pp. 9-17.
Hayashi, Tamio; Kabeta, Keiji; Yamamoto, Tsunehiro; Tamao, Kohei; Kumada, Makoto: "Optically Active Cyclic Allylsilanese Preparation by Asymmetric Hydrosilylation and Anti Stereochemistry in $S_E^1$ Reactions", *Tetrahedron Letters*, vol. 24, No. 50 (1983) pp. 5661-5664.
Mironov, V.F.; Maksimova, N.G.; Nepomnina, V.V. Izv. Akad. Nauk SSSR. Ser. chim. 1967, pp. 329-333. Document in Russian.

*Primary Examiner*—Samuel Barts
(74) *Attorney, Agent, or Firm*—Frommer Lawrence & Haug LLP; Ronald R. Santucci

(57) ABSTRACT

The present invention relates to (2-cyclopentenyl)chlorosilane derivatives and the preparation method thereof. In particular, it relates to a very economical process which reacts cyclopentadiene, which is formed by a cracking of industrially produced low-priced dicyclopentadiene, with a silane compound containing silicon-hydrogen bonds at elevated temperature in a hydrocarbon compound with a boiling point of a predetermined range, thus also enabling to prevent problematic production of dicyclopentadiene polymer by using the hydrocarbon compound. Further, in the presence of a group 10 metal compound catalyst, the process herein is capable of lowering the reaction temperature and increasing the yield in the reaction of sterically hindered alkyl-dichlorosilane. The (2-cyclopentenyl)chlorosilane may be useful in preparing an organic silicon compound containing an unsaturated group or a functional silicone polymer using the same, or in modifying the surface or manufacturing a thin layer.

12 Claims, No Drawings

(2-CYCLOPENTENYL)CHLOROSILANES AND THEIR PREPARATION METHODS

This application claims priority benefits from Korean Patent Application No. 10-2006-0014587 filed Feb. 15, 2006.

TECHNICAL FIELD

The present invention relates to (2-cyclopentenyl)chlorosilane derivatives and the preparation method thereof. In particular, it relates to a very economical process which reacts cyclopentadiene, which is formed by a cracking of industrially produced low-priced dicyclopentadiene, with a silane compound containing silicon-hydrogen bonds at elevated temperature in a hydrocarbon compound with a boiling point of a predetermined range, thus also enabling to prevent problematic production of dicyclopentadiene polymer by using a hydrocarbon compound. Further, in the presence of a group 10 metal compound catalyst, the process herein is capable of lowering the reaction temperature and increasing the yield in the reaction of sterically hindered alkyl dichlorosilane. The (2-cyclopentenyl)chlorosilane may be useful in preparing an organic silicon compound containing an unsaturated group or a functional silicone polymer using the same, or in modifying the surface or manufacturing a thin film.

RELATED PRIOR ART

Generally, organic silane containing a cyclopentenyl group, an unsaturated cyclic group, is synthesized by using as a raw material cyclopentadiene obtained by thermal cracking of dicyclopentadiene, which raises prime cost and lowers economical efficiency.

As a known method to prepare organic silane including cyclopentenyl group, Mironov et al. reported in 1967 that (2-cyclopentenyl)trichlorosilane (51%) was obtained by reacting cyclopentadiene with trichlorosilane at 240-250° C. for 5 hours in the presence of hexachloroplatinic acid catalyst, and that (2-cyclopentenyl)dichlorosilane (54%) was also obtained by using methyldichlorosilane [Mironov, V. F.; Maksimova, N. G.; Nepomnina, V. V. Izv. Akad. Nauk SSSR, Ser. chim. 1967, 329-33].

Hetflejs, J. and Vaisarova, V. (Czech.) reported that (2-cyclopentenyl)trichlorosilane (80-85%) was obtained by performing a reaction at 100-120° C. of cyclopentadiene and trichlorosilane [Hetflejs, J.; Vaisarova, V. Czech. Patent 171581 (1978), 171582 (1978)].

In 1972, Kumada et al. reported that (2-cyclopentenyl) trichlorosilane (69-81%) was selectively obtained by reacting cyclopentadiene with trichlorosilane at 120° C. for 58 hours in the presence of the catalyst of trialkylphosphine, methyldiphenylphosphine, neo-methyl-diphenylphosphine and Pd complex [Kiso, Y.; Yamamoto, K.; Tamao, K.; Kumada, M. J. Am. Chem. Soc. 1972, 94, 4373-4, Yamamoto, K.; Kiso, Y.; Ito, R.; Tamao, K.; Kumada, M. J. Organomet. Chem. 1981, 210, 9-17].

Further, they have also reported that (2-cyclopentenyl) methyldichlorosilane (87%) was obtained by reacting cyclopentadiene with methyldichlorosilane at 30° C. for 20 hours in the presence of the catalyst of dichloro[(R)-N,N-dimethyl-1{(S)-2-(diphenylphosphino)ferrocenyl}ethylamine] palladium(II)] [Hayashi, T.; Kabeta, K.; Yamamoto, T.; Tamao, K.; Kumada, M. Tetrahedron Lett. 1983, 24, 5661-4].

Meanwhile, Oshima and Tajima in 1978 reported that 91% yield was accomplished by reacting cyclopentadiene with trichlorosilane at 80° C. for 6 hours in the presence of $PdCl_2$ and $PPh_3$ [Iwao, O.; Miyoko, T. Japanese Pat. 1978-105464].

In 1990, Hayashi and Ito et al reported that (2-cyclopentenyl)trichlorosilane (73%) was obtained by reacting cyclopentadiene with trichlorosilane at 25° C. for 90 hours or at 80° C. for 20 hours in the presence of Pd complex of chiral ferrocenylphosphine [Hayashi, T.; Matsumoto, Y.; Morikawa, I.; Ito, Y. Tetrahedron: Asymetry, 1990, 1, 151-4].

As described above, all the conventional methods have employed expensive cyclopentadiene as a starting material in the presence of a Pt or Pd catalyst. As such, it has been general to use an expensive cyclopentadiene and Pd-phosphine catalyst instead of a Pt-based catalyst in hydrosilylation reaction.

Further, it is known that utilization of phosphine ligand having chirality is preferable to control the stereoselectivity of products [Marinetti, A. Tetrahedron Letters 1994, 35, 5861-4].

However, the conventional methods have a drawback in using expensive cyclopentadiene instead of dicyclopentadiene. That is, a cyclopentadiene molecule undergoes Diels-Alder reaction (or [4+2] cycloaddition reaction) with another cyclopentadiene molecule to form dicyclopentadiene at room temperature. Thus, it requires additional thermal cracking and an equipment to transform dicyclopentadiene to cyclopentadiene, and should be stored at a low temperature because it is susceptible to natural transformation into dicyclopentadiene. Further, the thermal treatment may cause a pipe to be choked by tar produced during the thermal cracking, which lowers the yield in a long-term continuous process.

To solve these problems, there have been made extensive researches. For example, Takayuki et al. in Nippon Zeon company reported that the process of preparing cyclopentadiene was performed for more than 400 hours by protecting (removing) the formation of the mixture of tar and polymer, which can be formed (produced) by self-[4+2] cycloaddition reaction of cyclopentadiene, using a hydrocarbon compound with high boiling point of above 300° C., followed by evaporation and cracking of dicyclopentadiene (and thermal treatment) [Takayuki, K.; Shinichiro, T. Jpn. Pat. 2002-226407].

However, there was no report that dicyclopentadiene was used as a starting material for preparing cyclopentenylsilane substituted with one silane group.

The present inventors made intensive researches and finally found that the utilization of a hydrocarbon compound with a boiling point of predetermined range may prevent the polymerization of dicyclopentadiene and produce silane containing cyclopentenyl group in higher yield, based on the findings that the researches of Voronkov et al., who studied reactions without using the aforementioned catalyst, resulted in low yield due to polymerization of dicyclopentadiene.

That is, the process here is superior in economical efficiency because it directly uses the industrially produced dicyclopentadiene without passing through a process of transforming into cyclopentadiene. Further, the process does not require a process for removing or recycling catalyst because the reaction herein may occur even in the absence of a catalyst.

Furthermore, in the presence of a group 10 metal compound catalyst, the process herein is capable of lowering the reaction temperature and increasing the yield in the reaction of sterically hindered alkyldichlorosilane.

Therefore, the present invention aims to provide a process for preparing a (2-cyclopentenyl)chlorosilane derivative, which is a novel organic silane compound containing a cyclopentenyl group, an unsaturated cyclic group.

DETAILED DESCRIPTION OF INVENTION

The present invention relates to a cyclopentenylchlorosilane derivative of formula (1):

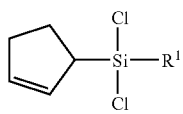
(1)

wherein $R^1$ is selected from the group consisting of a hydrogen atom, a halogen atom, a C1-C6 alkyl group, a C4-C7 cycloalkyl group and a phenyl group.

Further, the present invention also relates to a process of preparing a cyclopentenylchlorosilane derivative of Formula (1), which comprises a step of performing a reaction of dicyclopentadiene with an organic silane compound of Formula (2) at an elevated temperature as described in Scheme 1:

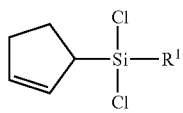
(1)

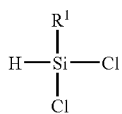
(2)

wherein $R^1$ is selected from the group consisting of a hydrogen atom, a halogen atom, a C1-C6 alkyl group, a C4-C7 cycloalkyl group and a phenyl group Scheme 1

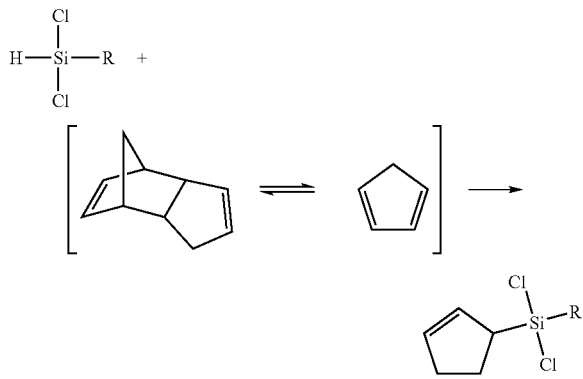

wherein $R^1$ is same as defined above.

Hereunder is provided a detailed description of the present invention.

The present invention relates to (2-cyclopentenyl)chlorosilane and a preparation method thereof, where an organic silane compound, such as low-priced dicyclopentadiene and industrially produced trichlorosilane ($HSiCl_3$), is used instead of conventionally used cyclopentadiene, which is unstable at room temperature, thus being superior from the economical point of view as well. The (2-cyclopentenyl) chlorosilane may be useful in preparing an organic silicon compound containing an intramolecular unsaturated group or a functional silicone polymer using the same, or in modifying the surface or manufacture thin films.

The process of the present invention is economical in that low-priced dicyclopentadiene and industrially produced organic silane compound are used instead of conventionally used expensive cyclopentadiene. The process herein is also advantageous in that it can be applied to a continuous process when a hydrocarbon compound having a boiling point of 30-400° C. is added for reaction at an elevated temperature, thus preventing decrease in yield as in conventional polymerization of dicyclopentadiene.

In particular, the present invention may employ the non-catalyst condition without any need to remove or recycle the catalysts. Further, in the presence of a group 10 metal compound catalyst, the process disclosed herein is capable of lowering the reaction temperature, increasing the yield in the reaction of sterically hindered alkyldichlorosilane, and easily purifying products by a simple vacuum distillation.

Furthermore, the process disclosed herein directly employs the industrially produced dicyclopentadiene unlike the conventional process using cyclopentadiene as a starting material, thus not necessitating the thermal decomposition and purification of dicyclopentadiene, thereby lowering prime cost. Further, the process herein is very economical in that it uses the industrially produced hydrochlorosilanes such as such as dichlorosilane ($H_2SiCl_2$), trichlorosilane ($HSiCl_3$), thus being very useful in synthesis of an organic silicon compound containing an unsaturated group and production of a functional silicone polymer.

Typical process of the present invention comprises: adding organic silane compound of Formula (2), dicyclopentadiene, hydrocarbon compound with a boiling point of 30-400° C. into pressure-resistant stainless steel reactor under nitrogen condition, sealing the reactor and performing a reaction.

The organic silane compound of Formula (2) is used in the amount of 1-10 moles, preferably 1-5 moles relative to one mole of dicyclopentadiene. Example of the organic silane compound include without limitation dichlorosilane, trichlorosilane, methyldichlorosilane, isopropyldichlorosilane, n-hexyldichlorosilane, cyclopentyldichlorosilane and phenyldichlorosilane.

Further, hydrocarbon compound with superior thermal stability may be used to prevent polymerization and tar generation from dicyclopentadiene in a volume ratio of 0.5-30 (vol/vol) relative to dicyclopentadiene.

Hydrocarbon compounds may be divided into two: hydrocarbon compounds with a higher boiling point as compared to dicyclopentadiene (>170° C.) and hydrocarbon compounds with a lower boiling point (<170° C.).

In particular, in case of using a hydrocarbon compound with a boiling point higher than that of dicyclopentadiene, it is preferable that the hydrocarbon has a boiling point of 170-400° C., preferably 200-350° C. or a mixture of at least one hydrocarbon compounds thereof may be used.

The structure of the hydrocarbon compound is not limited as long as its boiling point is within the aforementioned range, and substituted or a non-substituted saturated or an unsaturated straight aliphatic hydrocarbon, a substituted or a non-substituted saturated or an unsaturated aromatic hydrocarbon may be used.

Examples of the hydrocarbon compound include without limitation a $C_{10}$-$C_{20}$ aliphatic hydrocarbon; a $C_6$-$C_{12}$ aromatic hydrocarbon; a $C_1$-$C_5$ aliphatic hydrocarbon substituted with a phenyl group; an aromatic hydrocarbon substituted with a C1-C5 alkyl group; biphenyl substituted with a C1-C5 alkyl group; trephine substituted with a C1-C5 alkyl group; and naphthalene substituted with a C1-C5 alkyl group; and a mixture thereof.

Specifically, hydrocarbons with a long chain such as decane, dodecane and hexadecane: hydrocarbon substituted with a phenyl group such as triphenyl methane, 1,1,2-triphenylethane and 1,1,1-triphenylethane; biphenyls substituted with an alkyl group such as diethylbiphenyl and triethylbiphenyl; triphenyls prepared by thermally condensing benzene such as o-triphenyl, m-triphenyl and p-triphenyl; triphenyls prepared by alkylation (or methylation) of the aforementioned triphenyls; naphthalene substituted with an alkyl group such as 1,2,3-trimethylnaphthalene and 1,2,5-trimethylnaphthalene; substituted benzenes such as divinyl benzene and divinyl toluene.

In the synthesis of cyclopentenylchlorosilane derivatives herein, the use of a hydrocarbon compounds with lower boiling point than dicyclopentenylchlorosilane derivatives may prevent the polymerization or production of tar, which may be caused by self [4+2]cycloaddition reaction of cyclopentadienne.

Hydrocarbon compounds with a boiling point of 30-170° C., preferably 60-150° C. may be used, and examples of the hydrocarbon compounds include a $C_3$-$C_{16}$ aliphatic hydrocarbon and a $C_6$-$C_{12}$ aromatic hydrocarbon, for example saturated aliphatic hydrocarbons such as n-pentane, i-pentane, n-hexane, n-heptane, n-octane and n-nonane and aromatic hydrocarbons such as benzene, toluene, ethylbenzene and xylene.

That is, hydrocarbon compounds with higher or lower boiling points than that of dicyclopentadiene may be appropriately selected, and the selected compound or a mixture thereof may be used as the hydrocarbon compound.

The process herein may be performed in the absence of a catalyst, or optionally may be performed in the presence of a group 10 metal compound catalyst, thus enabling to obtain sterically hindered silane compounds.

Examples of the catalyst, which is a group 10 metal, include without limitation nickel, palladium, platinum or a ligand compound thereof such as chloride or phosphine compound.

That is, a catalyst herein may be selected from the group consisting of a group 10 metal atom, a group 10 metal chloride compound and a group 10 metal phosphine compound, and the phosphine compound may be selected from compounds of Formula (3) or (4) below.

P($R^2R^3R^4$)                                                     (3)

wherein $R^2$, $R^3$ and $R^4$ may be independently selected from the group consisting of a C1-C12 alkyl group, a phenyl group and an aromatic group substituted with A C1-C6 alkyl group, or two moieties selected out of $R^2$, $R^3$ and $R^4$ may be covalently bound to each other, thereby forming a 5-7 membered ring;

($R^2R^3$)P—Y—P($R^4R^5$)                              (4)

wherein Y is selected from the group consisting of a $C_1$-$C_{12}$ alkylene, an aromatic group and an aromatic group substituted with a C1-C6 alkyl group; $R^2$, $R^3$, $R^4$ and $R^5$ may be independently selected from the group consisting of a C1-C12 alkyl group, a phenyl group and an aromatic group containing a C1-C6 alkyl group, or two moieties selected out of $R^2$, $R^3$, $R^4$ and $R^5$ may be covalently bound to each other, thereby forming a 5-7 membered ring.

The catalyst may be a non-supported catalyst or a supported catalyst, which is a group 10 metal bound to a support. As the support, silicone resin, silica, a zeolite, other inorganic resin (polymer) or an organic polymer may be used.

Under a non-catalyst condition, the reaction is preferably performed at 150-350° C., more preferably 200-250° C. for about 1-3 hours.

Under a catalyst condition, the catalyst may be used in a catalytic amount, for example in 0.01-10 mol % relative to the organic silane compound. The reaction is performed at 150-250° C., preferably 150-200° C. for 1-3 hours.

After the termination of reaction, the reactor tube was immersed in water and cooled, and target compounds may be easily obtained by simple vacuum distillation of reactants.

The reaction may be performed in an autoclave or by continuously reacting dicyclopentadiene with organic silane compounds of Formula (2) at atmosphere or high pressure.

The cyclopentenylchlorosilane derivatives of Formula (1) herein may be used to prepare various silane compounds as described in Examples, or may be used as a raw material for preparing various silicone polymers or silane coupling agents or for surface modification or manufacturing thin films.

As set forth above, the process here is superior in economical efficiency because it directly uses the industrially produced dicyclopentadiene without going through a process of transforming into cyclopentadiene. Further, the process does not requires a process for removing or recycling catalyst because the reaction herein may occur even in the absence of a catalyst. Furthermore, in the presence of a group 10 metal compound catalyst, the process herein is capable of lowering the reaction temperature and increasing the yield in the reaction of sterically hindered alkyldichlorosilane.

Considering these aspects, the present invention is very economical and efficient as compared to conventional method, may be used in synthesis of various organic silicon compounds at a lower cost. Thus obtained monomer may be widely used to synthesize an organic silicone polymer.

EXAMPLES

The present invention is described more specifically by the following Examples. Examples herein are meant only to illustrate the present invention, but they should not be construed as limiting the scope of the claimed invention.

Example 1

Reaction with Dicyclopentadiene and Trichlorosilane

A reactor of 300 mL stainless steel tube was dried under nitrogen. 15.0 g (0.113 mol) of dicyclopentadiene, 122.4 g (0.904 mol) of trichlorosilane, 51 mL of toluene, 17 mL of hexadecane were added in the reactor. The reactor was sealed and the reaction was performed at 250° C. for 1 hour. The termination of reaction was verified by gas chromatography (GC/TCD). Products were subject to simple vacuum distillation, thereby providing a mixture (203.6 g) of (2-cyclopentenyl)trichlorosilane (34.4 g, 76%), 1,3-bis(trichlorosilyl)cyclopentane (1.4%), unreacted trichlorosilane, toluene and hexadecane.

Products separated from fractional vacuum distillation were identified by the analysis of MS (mass spectroscopic) data and NMR data.

(2-cyclopentenyl)trichlorosilane ($^1$H-NMR, CDCl$_3$, ppm): 2.13-2.25(m, 2H, CH$_2$CH$_2$CH), 2.43-2.51(m, 2H, CH$_2$CH$_2$CH), 2.66-2.75(m, 1H, CH$_2$CH$_2$CH), 5.77-5.72, 5.93-5.97(m, 2H, CH=CH)

Example 2

Reaction with Dicyclopentadiene and Dichlorosilane

As described in Example 1, 0.909 g (0.00688 mol) of dicyclopentadiene, 4.17 g (0.0413 mol) of dichlorosilane, 5 mL of toluene and 2 mL of hexadecane were placed in a reactor. The reactor was sealed and the reaction was performed at 250° C. for 1 hour. Products were subject to simple vacuum distillation, thereby providing a mixture (9.09 g) of (2-cyclopentenyl)dichlorosilane (1.2 g, 51.0%), unreacted dichlorosilane, toluene and hexadecane.

(2-cyclopentenyl)dichlorosilane ($^1$H-NMR, CDCl$_3$, ppm): 2.04-2.24(m, 2H, CH$_2$CH$_2$CH), 2.40-2.47(m, 2H, CH$_2$CH$_2$CH), 2.49-2.55(m, 1H, CH$_2$CH$_2$CH), 5.37(d, J=1.5 Hz, 1H, SiH), 5.67-5.71, 5.88-5.92(m, 2H, CH=CH)

Example 3

Reaction with Dicyclopentadiene and Methyldichlorosilane

As described in Example 2, 1.49 g (0.0113 mol) of dicyclopentadiene, 10.79 g (0.0902 mol) of methyldichlorosilane, 5 mL of toluene and 2 mL of hexadecane were placed in a reactor. The reactor was sealed and the reaction was performed at 250° C. for 1 hour. Products were subject to simple vacuum distillation, thereby providing a mixture (15.99 g) of (2-cyclopentenyl)methyldichlorosilane (1.2 g, 29%), unreacted methyldichlorosilane, toluene and hexadecane.

(2-cyclopentenyl)methyldichlorosilane ($^1$H-NMR, CDCl$_3$, ppm): 0.72(s, 3H, CH$_3$), 2.00-2.21(m, 2H, CH$_2$CH$_2$CH), 2.38-2.43(m, 2H, CH$_2$CH$_2$CH), 2.44-2.49(m, 1H, CH$_2$CH$_2$CH), 5.67-5.71, 5.83-5.87(m, 2H, CH=CH)

Example 4

Reaction with Dicyclopentadiene and Isopropyldichlorosilane

As described in Example 2, 1.98 g (0.0150 mol) of dicyclopentadiene, 12.91 g (0.0902 mol) of isopropyldichlorosilane, 5 mL of toluene and 2 mL of hexadecane were placed in a reactor. The reactor was sealed and the reaction was performed at 250° C. for 1 hour. Products were subject to simple vacuum distillation, thereby providing a mixture (18.47 g) of (2-cyclopentenyl)isopropyldichlorosilane (1.5 g, 24.3%), unreacted isopropyldichlorosilane, toluene and hexadecane.

(2-cyclopentenyl)isopropyldichlorosilane ($^1$H-NMR, CDCl$_3$, ppm): 1.13 (s, 3H, CCH$_3$), 1.15 (s, 3H, CCH$_3$), 1.30-1.40(m, 1H, CH$_3$CH), 2.06-2.22(m, 2H, CH$_2$CH$_2$CH), 2.41-2.56(m, 2H, CH$_2$CH$_2$CH), 2.41-2.56(m, 1H, CH$_2$CH$_2$CH), 5.68-5.71, 5.83-5.86(m, 2H, CH=CH)

Example 5

Reaction with Dicyclopentadiene and Cyclopentyldichlorosilane

As described in Example 2, 1.90 g (0.0150 mol) of dicyclopentadiene, 14.89 g (0.0880 mol) of cyclopentyldichlorosilane, 5 mL of toluene and 2 mL of hexadecane were placed in a reactor. The reactor was sealed and the reaction was performed at 250° C. for 1 hour. Products were subject to simple vacuum distillation, thereby providing a mixture (21.96 g) of (2-cyclopentenyl)cyclopentyldichlorosilane (1.4 g, 21.4%), unreacted cyclopentyldichlorosilane, toluene and hexadecane.

(2-cyclopentenyl)cyclopentyldichlorosilane ($^1$H-NMR, CDCl$_3$, ppm): 1.48-1.90(m, 9H, cyclopentyl H), 2.06-2.20(m, 2H, CH$_2$CH$_2$CHCH=CH), 2.40-2.54(m, 2H, CH$_2$CH$_2$CHCH=CH), 2.40-2.54(m, 1H, CH$_2$CH$_2$CHCH=CH), 5.68-5.72, 5.81-5.85(m, 2H, CH=CH)

Example 6

Reaction with Dicyclopentadiene and Phenyldichlorosilane described 1.97 g (0.0149 mol) of dicyclopentadiene, 15.8 g (0.0894 mol) of phenyldichlorosilane, 5 mL of toluene were placed in a reactor. Hexadecane was not added because it has a similar boiling point as a target product. The reactor was sealed, and the reaction was performed at 250° C. for 1 hour. Products were subject to simple vacuum distillation, thereby providing a mixture (12.2 g) of (2-cyclopentene) phenyldichlorosilane (2.8 g, 39.0%), unreacted phenyldichlorosilane and toluene.

(2-cyclopentene)phenyldichlorosilane ($^1$H-NMR, CDCl$_3$, ppm): 2.07-2.98(m, 2H, CH$_2$CH$_2$CH), 2.23-2.42(m, 2H, CH$_2$CH$_2$CH), 2.68-2.75(m, 1H, CH$_2$CH$_2$CH), 5.73-5.76, 5.84-5.87(m, 2H, CH=CH), 7.43-7.53, 7.74-7.76(m, 5H, PhH)

Example 7

Process for Continuous Reaction with Dicyclopentadiene and Trichlorosilane 3.01 g (0.0238 mol) of dicyclopentadiene, 18.8 g (0.139 mol) of trichlorosilane and 6 mL of hexadecane were placed in a reactor for continuous process as described below. The reactor was sealed, and a reaction was performed at 380° C. by adding reagents at a speed of 0.1 mL/min. The termination of the reaction was verified with gas chromatography (GC/TCD). Products were subject to simple vacuum distillation, thereby providing a mixture (27.9 g) of (2-cyclopentenyl)trichlorosilane (1.92 g, 21.0%), unreacted trichlorosilane and hexadecane.

Reactor for Continuous Process:

3-neck flask (500 mL) was equipped with a reactor and fluxing condenser. The centered reactor was prepared by installing heating coils around Pyrex glass tube (inner diameter: 21 mm, height: 400 mm). Thermal couple (K type, Chromel-Alumel) was immersed in mid of the reactor, and connected to an automatic temperature controller (Han Young Electronic Co., Ltd., model DX4, PID controller).

Reactants were mixed and introduced into the reactor at a constant rate by using a syringe pump [PTFE-Tubing Pump Heads (model no. 77390-00)/Standard digital drive (model no. 07523-60), Masterflex]. The reagents were introduced through the upper part of the reactor and products were excharged from the lower part of the reactor. To maintain the temperature of the condenser at −20° C., a mixture of water and anti-freezing solution (50:50 vol/vol) was circulated by using a low temperature circulated bath (model Lauda RE107).

Example 8

Reaction with Dicyclopentadiene and Methyldichlorosilane in the Presence of $PdCl_2/PBu_3$ Catalyst As described in Example 2, 2.87 g (0.0217 mol) of dicyclopentadiene, 3.74 g (0.0326 mol) of methyldichlorosilane, 0.036 g (0.000203 mol) of palladium dichloride, 100 μL (0.000406 mol) of tributylphosphine, 4 mL of toluene and 2 mL of hexadecane were placed in a reactor. The reactor was sealed and the reaction was performed at 180° C. for 1 hour. Products were subject to simple vacuum distillation, thereby providing a mixture (11.4 g) of (2-cyclopentenyl)methyldichlorosilane (4.3 g, 72%), other unreacted reactants, toluene, hexadecane, and unidentified compounds.

Example 9

Reaction with Dicyclopentadiene and Isopropyldichlorosilane in the Presence of $PdCl_2/PBu_3$ Catalyst As described in Example 2, 2.88 g (0.0218 mol) of dicyclopentadiene, 4.67 g (0.0326 mol) of isopropyldichlorosilane, 0.036 g (0.000203 mol) of palladium dichloride, 100 μL (0.000406 mol) of tributylphosphine and 4 mL of toluene and 2 mL of hexadecane were placed in a reactor. The reactor was sealed and the reaction was performed at 180° C. for 1 hour. Products were subject to simple vacuum distillation, thereby providing a mixture (11.4 g) of (2-cyclopentenyl)isopropyldichlorosilane (4.81 g, 71%), other unreacted reactants, toluene, hexadecane, and unidentified compounds.

Example 10

Reaction with Dicyclopentadiene and Cyclopentyldichlorosilane in the Presence of $PdCl_2/PBu_3$ Catalyst As described in Example 2, 2.97 g (0.0225 mol) of dicyclopentadiene, 5.66 g (0.0335 mol) of isopropyldichlorosilane, 0.036 g (0.000203 mol) of palladium dichloride, 100 μL (0.000406 mol) of tributylphosphine and 4 mL of toluene and 2 mL of dodecane were placed in a reactor. The reactor was sealed, and the reaction was performed at 180° C. for 1 hour. Products were subject to simple vacuum distillation, thereby providing a mixture (13.4 g) of (2-cyclopentenyl)cyclopentyldichlorosilane (5.73 g, 73%), other unreacted reactants, toluene, hexadecane, and unidentified compounds.

Example 11

Reaction with Dicyclopentadiene and Methyldichlorosilane in the Presence of $PdCl_2/PBu_3$ Catalyst After a reactor of 150 mL stainless steel tube was cooled under the dried nitrogen condition, 26.37 g (0.199 mol) of dicyclopentadiene, 34.34 g (0.299 mol) of methyldichlorosilane, 0.036 g (0.000203 mol) of palladium dichloride, 100 μL (0,000406 mol) of tributylphosphine and 30 mL of toluene and 10 mL of hexadecane were placed in a reactor. The reactor was sealed and the reaction was performed at 180° C. for 1 hour. Products were subject to simple vacuum distillation, thereby providing a mixture (98.3 g) of (2-cyclopentenyl)methyldichlorosilane (43.3 g, 80%), other unreacted reactants, toluene, hexadecane, and unidentified compounds.

Example 12

Reaction with Dicyclopentadiene and Methyldichlorosilane in the Presence of $PdCl_2/PPh_3$ Catalyst As described in Example 2, 2.86 g (0.0216 mol) of dicyclopentadiene, 4.97 g (0.0432 mol) of methyldichlorosilane, 0.051 g (0.000288 mol) of palladium dichloride, 86 μL (0.000267 mol) of tributylphosphine and 4 mL of toluene and 2 mL of hexadecane were placed in a reactor. The reactor was sealed and the reaction was performed at 180° C. for 1 hour. Products were subject to simple vacuum distillation, thereby providing a mixture (10.0 g) of (2-cyclopentenyl)methyldichlorosilane (0.9 g, 12%), other unreacted reactants, toluene, hexadecane, and unidentified compounds.

Example 13

Reaction with Dicyclopentadiene and Methyldichlorosilane in the Presence of $NiCl_2/PBu_3$ Catalyst As described in Example 2, 3.01 g (0.0228 mol) of dicyclopentadiene, 5.19 g (0.0451 mol) of methyldichlorosilane, 0.032 g (0.000247 mol) of nickel dichloride, 57 μL (0.000230 mol) of tributylphosphine and 4 mL of toluene and 2 mL of hexadecane were placed in a reactor. The reactor was sealed and the reaction was performed at 180° C. for 1 hour. Products were subject to simple vacuum distillation, thereby providing a mixture (11.8 g) of (2-cyclopentenyl)methyldichlorosilane (3.1 g, 38%), other unreacted reactants, toluene, hexadecane, and unidentified compounds.

Example 14

Reaction with Dicyclopentadiene and Methyldichlorosilane in the Presence of $PdCl_2$/1,4-bis(diphenylphosphino)butane Catalyst As described in Example 2, 2.85 g (0.0216 mol) of dicyclopentadiene, 3.72 g (0.0323 mol) of methyldichlorosilane, 0.040 g (0.000226 mol) of palladium dichloride, 0.19 g (0.000451 mol) of 1,4-bis(diphenylphosphino)butane and 4 mL of toluene and 2 mL of hexadecane were placed in a reactor. The reactor was sealed and the reaction was performed at 180° C. for 2 hours. Products were subject to simple vacuum distillation, thereby providing a mixture (13.2 g) of (2-cyclopentenyl)methyldichlorosilane (4.1 g, 70%), other unreacted reactants, toluene, hexadecane, and unidentified compounds.

Example 15

Reaction with Dicyclopentadiene and Methyldichlorosilane in the Presence of Pd on Charcoal Catalyst As described in Example 2, 2.92 g (0.0221 mol) of dicyclopentadiene, 3.79 g (0.0331 mol) of methyldichlorosilane, 0.0602 g ≅1% Pd on Charcoal, 86 μL (0.000267 mol) of tributylphosphine and 4 mL of toluene and 2 mL of hexadecane were placed in a reactor. The reactor was sealed and the reaction was performed at 180° C. for 1 hour. Products were subject to simple vacuum distillation, thereby providing a mixture (12.8 g) of (2-cyclopentenyl)methyldichlorosilane (3.8 g, 63%), other unreacted reactants, toluene, hexadecane, and unidentified compounds. Besides, tetrakis(triphenylphosphine)palladium also showed catalyst effect.

As described above, the present invention relates to a process of preparing (2-cyclopentenyl)chlorosilane derivatives in the absence of a catalyst, which comprises a step of reacting dicyclopentadiene and a compound containing hydrogen-silicon bonds. Optionally, the reaction may be performed in the presence of a group 10 metal compound catalyst to selectively provide an organic silane compound which contains a cyclopentenyl group, an unsaturated cyclic compound. As compared to the conventional method, the process disclosed herein requires neither the thermal decomposition of dicyclopentadiene nor the removal or recycling of the catalyst. Further, in the presence of a group 10 metal compound catalyst, the process disclosed herein is capable of lowering the reaction temperature and increasing the yield in the reaction of sterically hindered alkyl dichlorosilane.

What is claimed is:

1. A process of preparing a cyclopentenylchlorosilane derivative of Formula (1), the process comprising a step of performing a reaction with dicyclopentadiene and an organic silane compound of Formula (2) at an elevated temperature:

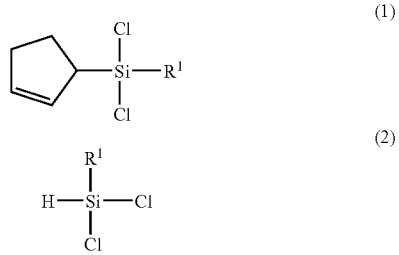

wherein $R^1$ is selected from the group consisting of a hydrogen atom, a halogen atom, a C1-C6 alkyl group, a C4-C7 cycloalkyl group and a phenyl group.

2. The process of claim 1, wherein the reaction is performed at 150-350° C.

3. The process of claim 1, wherein the reaction is performed in the presence of at least one hydrocarbon compound with a boiling point of 30-400° C.

4. The process of claim 3, wherein the hydrocarbon compound is selected from the group consisting of $C_5$-$C_{20}$ aliphatic hydrocarbon; $C_6$-$C_{12}$ aromatic hydrocarbon; $C_1$-$C_5$ aliphatic hydrocarbon substituted with a phenyl group; aromatic hydrocarbon substituted with a $C_1$-$C_5$ alkyl group; biphenyl substituted with a $C_1$-$C_5$ alkyl group; triphenyl substituted with a $C_1$-$C_5$ alkyl group; and naphthalene substituted with a $C_1$-$C_5$ alkyl group.

5. The process of claim 3, wherein the hydrocarbon compound is used in a volume ratio of 0.5-30 (vol/vol) relative to the dicyclopentadiene.

6. The process of claim 1, wherein the reaction is performed in the absence of a catalyst or in the presence of a group 10 metal compound catalyst.

7. The process of claim 6, wherein the catalyst is selected from the group consisting of group 10 metal atom, group 10 metal chloride and group 10 metal phosphine compound.

8. The process of claim 7, wherein the phosphine compound is a compound of Formula 3 or 4:

$$P(R^2R^3R^4) \qquad (3)$$

wherein $R^2$, $R^3$ and $R^4$ may be independently selected from the group consisting of a $C_1$-$C_{12}$ alkyl group, a phenyl group and an aromatic group substituted with A C1-C6 alkyl group, or two moieties selected out of $R^2$, $R^3$ and $R^4$ may be covalently bound to each other, thereby forming a 5-7 membered ring;

$$(R^2R^3)P—Y—P(R^4R^5) \qquad (4)$$

wherein Y is selected from the group consisting of a $C_1$-$C_{12}$ alkylene, an aromatic group and an aromatic group substituted with a C1-C6 alkyl group; $R^2$, $R^3$, $R^4$ and $R^5$ may be independently selected from the group consisting of a C1-C12 alkyl group, a phenyl group and an aromatic group containing a $C_1$-$C_6$ alkyl group, or two moieties selected out of $R^2$, $R^3$, $R^4$ and $R^5$ may be covalently bound to each other, thereby forming a 5-7 membered ring.

9. The process of claim 6, wherein the catalyst is a non-supported catalyst or a supported catalyst.

10. The process of claim 9, wherein the support is selected from the group consisting of silicone resin, silica, a zeolite, other inorganic resin (polymer) and an organic polymer.

11. The process of claim 7, wherein the catalyst is used in the amount of 0.01-10 mol % relative to the organic silane compound of Formula (2).

12. The process of claim 9, wherein the catalyst is used in the amount of 0.01-10 mol % relative to the organic silane compound of Formula (2).

* * * * *